(12) United States Patent
Sherman et al.

(10) Patent No.: US 12,318,269 B2
(45) Date of Patent: Jun. 3, 2025

(54) MEDICAL ARTICLES WITH RADIO OPAQUE PATTERNS

(71) Applicant: Solventum Intellectual Properties Company, Maplewood, MN (US)

(72) Inventors: Audrey A. Sherman, Woodbury, MN (US); Tony J. Kaufman, Rosemount, MN (US); David A. Cadalbert, Jr., Baldwin, WI (US)

(73) Assignee: Solventum Intellectual Properties Company, Maplewood, MN (US)

( * ) Notice: Subject to any disclaimer, the term of this patent is extended or adjusted under 35 U.S.C. 154(b) by 513 days.

(21) Appl. No.: 17/639,650

(22) PCT Filed: Aug. 18, 2020

(86) PCT No.: PCT/IB2020/057771
§ 371 (c)(1),
(2) Date: Mar. 2, 2022

(87) PCT Pub. No.: WO2021/048660
PCT Pub. Date: Mar. 18, 2021

(65) Prior Publication Data
US 2022/0296436 A1    Sep. 22, 2022

Related U.S. Application Data

(60) Provisional application No. 62/898,161, filed on Sep. 10, 2019.

(51) Int. Cl.
*A61F 13/44*     (2006.01)
*A61F 13/15*     (2006.01)
(Continued)

(52) U.S. Cl.
CPC ........ *A61F 13/44* (2013.01); *A61F 13/15723* (2013.01); *A61F 13/15747* (2013.01);
(Continued)

(58) Field of Classification Search
CPC .......... A61F 13/15723; A61F 13/15747; A61F 13/36; A61F 13/44; A61F 2013/1591;
(Continued)

(56) References Cited

U.S. PATENT DOCUMENTS 2,698,270 A   12/1954   Mesek
3,965,907 A   6/1976    Hardy
(Continued)

FOREIGN PATENT DOCUMENTS

CA         1064240      10/1979
CN        205019264     2/2016
(Continued)

OTHER PUBLICATIONS

International Search Report for PCT Application No. PCT/IB2020/057771, mailed on Oct. 15, 2020, 5 pages.

*Primary Examiner* — Dani Fox
*Assistant Examiner* — Soorena Kefayati

(57) ABSTRACT

Absorbent medical articles include a first absorbent layer with a radio opaque element located on the surface of the first absorbent layer. The radio opaque element has at least one segment that is non-linear and has at least one vertex, the vertex defines an angle of at least 15° and less than 165°. The radio opaque element may be a continuous or discontinuous element. The absorbent medical article may include additional absorbent layers. The radio opaque element makes the absorbent medical article detectable if left inside a patient.

17 Claims, 2 Drawing Sheets

(51) Int. Cl.
*A61F 13/36* (2006.01)
*A61F 13/84* (2006.01)

(52) U.S. Cl.
CPC ...... *A61F 13/36* (2013.01); *A61F 2013/1591* (2013.01); *A61F 2013/8497* (2013.01)

(58) Field of Classification Search
CPC .............. A61F 2013/8497; A61L 15/44; A61L 2300/44; A61L 26/0066; A61L 31/18; A61B 6/12
See application file for complete search history.

(56) References Cited

U.S. PATENT DOCUMENTS

| | | | | |
|---|---|---|---|---|
| 4,244,369 | A * | 1/1981 | McAvinn | A61F 13/44 604/362 |
| 4,798,581 | A | 1/1989 | Jessup | |
| 4,813,062 | A | 3/1989 | Gilpatrick | |
| 4,938,901 | A * | 7/1990 | Groitzsch | D04H 3/16 604/362 |
| 5,456,718 | A * | 10/1995 | Szymaitis | A61B 5/06 604/362 |
| 6,356,621 | B1 | 3/2002 | Furumori | |
| 6,520,184 | B2 * | 2/2003 | Bonnassieux | A61B 46/40 128/849 |
| 10,461,397 | B2 * | 10/2019 | Augustine | A61B 90/98 |
| 2005/0049564 | A1 * | 3/2005 | Fabian | A61F 13/44 604/362 |
| 2007/0276477 | A1 * | 11/2007 | Lee | A61F 2/82 623/23.72 |
| 2008/0138387 | A1 * | 6/2008 | Machiraju | A61L 31/16 602/44 |
| 2009/0264385 | A1 * | 10/2009 | Crowley | A61K 9/006 514/315 |
| 2011/0071499 | A1 * | 3/2011 | Hakimimehr | A61K 9/7084 604/509 |
| 2011/0165373 | A1 * | 7/2011 | Khandkar | G21F 1/12 156/60 |
| 2012/0071846 | A1 * | 3/2012 | Shao | B32B 5/022 156/60 |
| 2014/0243770 | A1 | 8/2014 | Stewart | |
| 2015/0032070 | A1 * | 1/2015 | Colby | A61F 13/44 604/385.01 |
| 2016/0008091 | A1 * | 1/2016 | Saotome | A61B 90/90 340/572.1 |
| 2016/0089274 | A1 * | 3/2016 | Hunter | A61F 13/36 604/362 |
| 2018/0000556 | A1 * | 1/2018 | Blair | A61F 13/44 |
| 2018/0333309 | A1 * | 11/2018 | Merritt | A61B 90/98 |
| 2018/0344429 | A1 * | 12/2018 | Stewart | A61B 90/36 |
| 2019/0015638 | A1 | 1/2019 | Gruba | |
| 2019/0074574 | A1 * | 3/2019 | Augustine | G06K 19/07758 |

FOREIGN PATENT DOCUMENTS

| | | |
|---|---|---|
| GB | 640541 | 7/1950 |
| GB | 839718 | 6/1960 |
| GB | 2169906 | 7/1986 |
| WO | 1996001096 | 1/1996 |
| WO | 1998010367 | 3/1998 |
| WO | 2010144024 | 12/2010 |

* cited by examiner

MEDICAL ARTICLES WITH RADIO OPAQUE PATTERNS

FIELD OF THE DISCLOSURE

This disclosure relates to medical articles that contain radio opaque patterns. These radio opaque patterns permit detection of medical articles left in a patient.

BACKGROUND

Surgical sponges and wipes are commonly used during surgical procedures to absorb body fluids of the patient both inside the incision and around the site of surgery. Sponges of this nature are usually made of an open-meshed absorbent fabric, such as woven cotton. It is important, of course, that all of such sponges be removed from the patient's body after surgery is complete and before the incision has been closed. Accordingly, it is a standard procedure for the surgical team to carefully count the sponges both before placement in the incision and after removal from the incision to reduce the possibility that a sponge may be left in the patient. As an additional safety measure, the sponges have been provided with a flexible insert which is opaque to X-rays. Radio opaque threads and strands have been the gold standard for incorporation into surgical sponges and gauze for 50+ years.

SUMMARY

This disclosure relates to medical articles that contain radio opaque patterns. These radio opaque patterns permit detection of medical articles left in a patient. Disclosed herein are absorbent medical articles, adhesive articles that can be used to make the absorbent medical articles, and methods of making the absorbent medical articles.

In some embodiments, the absorbent medical article comprises a first absorbent layer with a first major surface and a second major surface, a second layer with a first major surface and a second major surface, and a radio opaque element located between the second major surface of the first absorbent layer and the first major surface of the second layer. The radio opaque element comprises at least one segment that is non-linear and having at least one vertex, wherein the vertex defines an angle of at least 15° and less than 165°. The radio opaque element may be a continuous or discontinuous element.

Also disclosed herein are adhesive articles comprising a first carrier layer with a first release surface, a second carrier layer with a second release surface, and a continuous or discontinuous radio opaque adhesive article located between the first release surface and the second release surface. The continuous or discontinuous radio opaque adhesive article comprises a radio opaque element comprising a radio opaque material, where the radio opaque element comprises at least one segment that is non-linear and has at least one vertex, wherein the vertex defines an angle of at least 15° and less than 165°.

Also disclosed are methods for preparing absorbent medical articles comprising providing a first absorbent layer with a first major surface and a second major surface, providing a continuous or discontinuous radio opaque adhesive article with a first major surface and a second major surface, and contacting the first major surface of the continuous or discontinuous radio opaque adhesive article to the second major surface of the first absorbent layer. The radio opaque element comprises at least one segment that is non-linear and has at least one vertex, wherein the vertex defines an angle of at least 15° and less than 165°, and comprising a radio opaque material.

BRIEF DESCRIPTION OF THE DRAWINGS

The present application may be more completely understood in consideration of the following detailed description of various embodiments of the disclosure in connection with the accompanying drawings.

Figure 1:
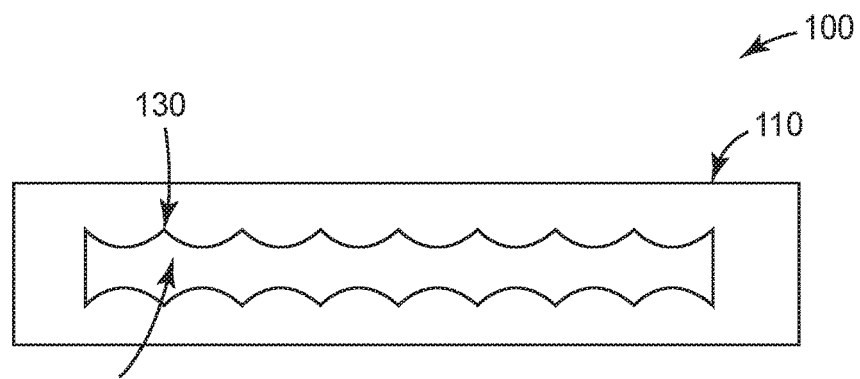
FIG. 1 is a top view of an embodiment of an article of the present disclosure.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Surgical sponges and wipes are commonly used during surgical procedures to absorb body fluids of the patient both inside the incision and around the site of surgery. Sponges of this nature are usually made of an open-meshed absorbent fabric, such as woven cotton. It is important, of course, that all of such sponges be removed from the patient's body after surgery is complete and before the incision has been closed. Accordingly, it is a standard procedure for the surgical team to carefully count the sponges both before placement in the incision and after removal from the incision to reduce the possibility that a sponge may be left in the patient.

In spite of such safety measures, sponges have been occasionally lost, particularly when an unexpected emergency disrupted the normal operative routine such as counting, which is subject to human error. When saturated by body fluids, such as blood, the sponges become significantly reduced in size and assume a color the same as some types of body tissue, thus making visual detection of the sponges extremely difficult. As a result, it has been required to provide the sponges with a flexible insert which is opaque to X-rays. Radio opaque threads and strands have been the gold standard for incorporation into surgical sponges and gauze for 50+ years.

In case of a disputed or non-tallying sponge count in the operating room, or in case of unexpected or unexplainable post-operative discomfort on the part of the patient, a portable X-ray unit is brought to the patient and an X-ray exposure should reveal the presence or absence of a lost sponge. A negative plate should be reassurance to the surgeon that he and his operative team have not left a sponge in the patient. Yet the ability to discern a simple radio opaque thread or yarn that has been crumpled up or twisted can be difficult and the thread could be mistaken for a twisted about portion of the patients' anatomy in the X-ray image.

In this disclosure, absorbent medical articles are described that have radio opaque patterns that are not linear like simple threads or strands but are two dimensional patterns that are not natural within the human body and therefore are more readily distinguished if present within a patient. Also disclosed are adhesive articles that can be used to prepare absorbent medical articles with radio opaque patterns, and methods of preparing absorbent medical articles with radio opaque patterns.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. For example, reference to "a layer" encompasses embodiments having one, two or more layers. As used in this specification and the appended claims, the term "or" is generally employed in its sense including "and/or" unless the content clearly dictates otherwise.

The term "adhesive" as used herein refers to polymeric compositions useful to adhere together two adherends. Examples of adhesives are pressure sensitive adhesives, heat activated adhesives, and hot melt adhesives.

Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

Heat activated adhesives are non-tacky at room temperature but become tacky and capable of bonding to a substrate at elevated temperatures. These adhesives usually have a Tg or melting point (Tm) above room temperature. When the temperature is elevated above the Tg or Tm, the storage modulus usually decreases and the adhesive become tacky. Like pressure sensitive adhesives, heat activated adhesives also have viscoelastic properties.

Hot melt adhesives are thermoplastic materials that are solid and non-tacky at room temperature but upon heating melt and flow. The hot melt adhesive is applied in the molten state and forms a bond upon cooling to a solid state.

The terms "Tg" and "glass transition temperature" are used interchangeably. If measured, Tg values are determined by Differential Scanning Calorimetry (DSC) at a scan rate of 10° C./minute, unless otherwise indicated. Typically, Tg values for copolymers are not measured but are calculated using the well-known Fox Equation, using the monomer Tg values provided by the monomer supplier, as is understood by one of skill in the art.

The term "room temperature" refers to ambient temperature, generally 20-22° C., unless otherwise noted.

The term "(meth)acrylate" refers to monomeric acrylic or methacrylic esters of alcohols. Acrylate and methacrylate monomers or oligomers are referred to collectively herein as "(meth)acrylates". Polymers described as "(meth)acrylate-based" are polymers or copolymers prepared primarily (greater than 50% by weight) from (meth)acrylate monomers and may include additional ethylenically unsaturated monomers.

The term "adjacent" as used herein when referring to two layers means that the two layers are in proximity with one another with no intervening open space between them. They may be in direct contact with one another (e.g. laminated together) or there may be intervening layers.

The terms "polymer" and "macromolecule" are used herein consistent with their common usage in chemistry. Polymers and macromolecules are composed of many repeated subunits. As used herein, the term "macromolecule" is used to describe a group attached to a monomer that has multiple repeating units. The term "polymer" is used to describe the resultant material formed from a polymerization reaction.

Disclosed herein are absorbent medical articles comprising a first absorbent layer with a first major surface and a second major surface, a second layer with a first major surface and a second major surface and a radio opaque element located between the second major surface of the first absorbent layer and the first major surface of the second layer. The radio opaque element comprises at least one segment that is non-linear and having at least one vertex, wherein the vertex defines an angle of at least 15° and less than 165°.

A wide range of absorbent layers are suitable for the first absorbent layer. Typically, the absorbent layer comprises fibrous materials. Examples of suitable fibrous materials include the natural cellulose-based materials such as the materials commonly known as "gauze" which may be made from fibers of cotton, rayon, polyester, or a combination thereof. A wide array of man-made fibrous materials has been developed for use in medical articles. These man-made fibrous materials may be woven or non-woven materials. Examples of useful fibrous materials include: alginic acid; polyolefin materials such as polyethylene and polypropylene; polyacrylonitrile; polyamides such as NYLON 6 and NYLON 66; polyesters such as polyethylene terephthalate (PET); polcarboxymethylcellulose (CMC), chitosan and chitosan derivatives such as carboxymethylchitosan; and cellulose ethyl sulfonate (CES).

The absorbent layers may be of any suitable thickness. Typically, the absorbent layer or layers are 127-2540 micrometers (5-100 mils) thick. More typically, the absorbent layers are 254-1270 micrometers (10-50 mils), or even 508-762 micrometers (20-30 mils) thick.

In some embodiments, the second layer comprises an absorbent layer that may be the same or different from the first absorbent layer. The second layer may comprise the same material as the first absorbent layer, and the second layer may be the same or a similar thickness to the first absorbent layer or it may be different. In some embodiments, the second absorbent layer may be a section of the first absorbent layer that has been folded over.

The absorbent medical article also comprises a radio opaque element located between the second major surface of the first absorbent layer and the first major surface of the second layer. Because the articles of the current disclosure are used in absorbent articles that are designed to come into contact with bodily fluids such as blood, the radio opaque element should not be soluble in or affected by bodily fluids. Therefore, the radio opaque elements and the components of these elements are insoluble or essentially insoluble in aqueous fluids.

The radio opaque elements may be positive elements or negative elements. Positive elements are those elements that are discrete solid elements with a shape that includes at least one vertex. Negative elements refer to elements where a shape that includes at least one vertex have been removed from an essentially continuous layer. In this way, the element is a void in a layer and not a solid material.

In some embodiments, the radio opaque element comprises a polymeric matrix with a radio opaque material dispersed therein. A wide range of polymeric matrices are suitable. In some embodiments, the polymeric matrix comprises an adhesive matrix. Typically, the adhesive matrix is selected from a hot melt adhesive, a heat activated adhesive, or a pressure sensitive adhesive. Each of these classes of adhesives are different and are differentiated by their properties. Pressure sensitive adhesives are viscoelastic materials and are permanently tacky at room temperature. Heat activated adhesives are similar to pressure sensitive adhesives, but are not tacky at room temperature, but rather become tacky at an elevated temperature, forming adhesive bonds at elevated temperature. Hot melt adhesives are a different class of materials, thermoplastic materials, that melt and flow, and form an adhesive bond upon cooling. Each of these classes of adhesives has different advantages and disadvantages.

Pressure sensitive adhesives in general include self-tacky materials or are a combination of an elastomeric polymer and a tackifier. Examples of suitable pressure sensitive adhesive materials include (meth)acrylate-based polymers, natural rubbers, synthetic rubbers such as nitrile rubbers, ethylene-vinyl acetate copolymers with high vinyl acetate content, silicone rubbers, and thermoplastic-elastomeric block copolymers. The same classes of materials are suitable for heat activated adhesives. Typically, heat activated adhesives have a higher Tg than pressure sensitive adhesives. Pressure sensitive adhesives typically have a Tg that is below room temperature, often 0° C. or lower, while heat activated adhesives have a Tg that is above room temperature, often 40° C. or higher.

A wide range of hot melt adhesives are suitable and are well known in the art. Examples of suitable hot melt adhesive include: ethylene-vinyl acetate (EVA) copolymers; ethylene-acrylate copolymers such as ethylene n-butyl acrylate (EnBA), ethylene-acrylic acid (EAA) and ethylene-ethyl acetate (EEA) as well as ethylene-vinylacetate-maleic anhydride and ethylene-acrylate-maleic anhydride terpolymers; polyolefins such as polyethylene (LDPE and HDPE), atactic polypropylene, or poly-1-butene; polyamides; polyesters; and polyurethanes.

If the adhesive layer is a pressure sensitive adhesive, the second layer may comprise a carrier layer. Examples of suitable carrier layers are release liners. Release liners are well understood articles in the adhesive arts and include at least one surface that is a release material surface, that is to say a surface containing material to which adhesives do not adhere strongly. In these embodiments, the carrier layer protects the pressure sensitive adhesive layer during storage or transportation. Typically, these articles are intermediate articles that are used to prepare different multi-layer articles. For example, the carrier layer can be removed to expose the pressure sensitive adhesive layer followed by contacting of the pressure sensitive adhesive layer to a second absorbent layer.

The radio opaque element also comprises a radio opaque material. A wide range of radio opaque materials are suitable. Among the suitable radio opaque materials are barium salts, bismuth salts, tungsten salts, and combinations thereof.

In some embodiments, the radio opaque element is an essentially continuous element with an array of segments that are non-linear and have at least one vertex, where the vertex defines an angle of at least 15° and less than 165°. In some embodiments, the array of segments is in the shape of a geometric object or indicia. A wide range of shapes are suitable, such as regular and irregular polygonal shapes such as triangles, squares, rectangles, pentagons, hexagons, heptagons, octagons, nonagons, decagons, and the like. The essentially continuous element may contain repeating features of the same shape, or the shapes may be different. For example, the essentially continuous element may contain an array of triangular segments interspersed between octagonal elements. Also, as mentioned above, the element may be a positive element (a shaped matrix) or a negative element (a shaped void in a matrix).

The essentially continuous element may also contain indicia, a term used in philately to indicate distinguishing marks, signs, or identifying marks. In philately, indicia are markings on a mail piece showing that postage has been prepaid by the sender. In modern usage, the term has come to refer to any symbol, notation or the like placed onto an article. Examples of indicia include numbers, letters, logos, and the like. In the current articles, the essentially continuous element may contain a warning message such as 'MEDICAL ARTICLE IS PRESENT", or logos such as "UNIVERSITY MEDICAL CENTER".

In other embodiments, the radio opaque element is an array of discrete units, wherein the units of the array may be the same or different, and wherein the discrete units are non-linear and have at least one vertex, wherein the vertex defines an angle of at least 15° and less than 165°, wherein the array of segments are in the shape of a geometric object or indicia. Discrete units are not connected together like the essentially continuous element described above. Suitable geometric objects and indicia are described above.

The radio opaque element may further comprise at least one additional additive comprising a colorant, a fluorescent agent, or a brightening agent. These additives can further assist in detecting the articles by providing optical detection methods. Colorants aid by making the articles more visible to the naked eye. The colorants may be pigments or dyes that make the radio opaque element a color that contrasts with the white color of the absorbent layers.

Fluorescent agents are ones that demonstrate fluorescence. Fluorescence is the emission of light by a substance that has absorbed light or other electromagnetic radiation. In most cases, the emitted light has a longer wavelength, and therefore lower energy, than the absorbed radiation. Fluorescent materials cease to glow nearly immediately when the radiation source stops, unlike phosphorescent materials, which continue to emit light for some time after.

Brightening agents, also called optical brighteners are chemical compounds that absorb light in the ultraviolet and violet region (usually 340-370 nm) of the electromagnetic spectrum, and re-emit light in the blue region (typically 420-470 nm) by fluorescence. A white surface treated with an optical brightener can emit more visible light than that which shines on it, making it appear brighter.

Thus, fluorescent agents and brightening agents function by absorbing radiation of one wavelength, such as UV light, and re-emitting light of different wavelength, typically a longer wavelength such that the re-emitted light falls into the visible wavelength range. In this way, a light source, such as a UV lamp, can be shined into an incision of a patient prior to closing the incision, and if any sponges or wipes are present the radio opaque element may be visibly detectable. This provides an additional level of detection for the articles.

Also disclosed herein are adhesive articles. In some embodiments, the adhesive article comprises a first carrier liner with a first release surface, a second carrier liner with a second release surface, and a continuous or discontinuous radio opaque adhesive article located between the first release surface and the second release surface. The continuous or discontinuous radio opaque adhesive article comprises a radio opaque element comprising a radio opaque material, wherein the radio opaque element comprises at least one segment that is non-linear and has at least one vertex, wherein the vertex defines an angle of at least 15° and less than 165°.

In some embodiments, the radio opaque adhesive article comprises an adhesive layer comprising a polymeric adhesive matrix with a radio opaque material dispersed therein. A wide range of polymeric adhesive matrices are suitable. Typically, the polymeric adhesive matrix is selected from a hot melt adhesive, a heat activated adhesive, or a pressure sensitive adhesive. Each of these classes of adhesives is described in detail above.

In some embodiments, the radio opaque adhesive article comprises a multi-layer article comprising a first adhesive matrix layer, a continuous or discontinuous radio opaque layer, and a second adhesive matrix layer. In this way the radio opaque layer is not dispersed within the adhesive matrix, rather the radio opaque layer is present between two adhesive matrix layers. The two adhesive matrix layers may be the same or different. Additionally, the two adhesive matrix layers may independently be pressure sensitive adhesives, heat activated adhesives, or hot melt adhesives, as are described above.

The radio opaque element also comprises a radio opaque material. A wide range of radio opaque materials are suitable. Among the suitable radio opaque materials are barium salts, bismuth salts, tungsten salts, and combinations thereof.

In some embodiments, the radio opaque element is an essentially continuous element with an array of segments that are non-linear and have at least one vertex, where the vertex defines an angle of at least 15° and less than 165°. In some embodiments, the array of segments is in the shape of a geometric object or indicia. A wide range of shapes are suitable, such as regular and irregular polygonal shapes such as triangles, squares, rectangles, pentagons, hexagons, heptagons, octagons, nonagons, decagons, and the like. The essentially continuous element may contain repeating features of the same shape, or the shapes may be different. For example, the essentially continuous element may contain an array of triangular segments interspersed between octagonal elements.

The essentially continuous element may also contain indicia, a term used in philately to indicate distinguishing marks, signs, or identifying marks. In philately, indicia are markings on a mail piece showing that postage has been prepaid by the sender. In modern usage, the term has come to refer to any symbol, notation or the like placed onto an article. Examples of indicia include numbers, letters, logos, and the like. In the current articles, the essentially continuous element may contain a warning message such as 'MEDICAL ARTICLE IS PRESENT", or logos such as "UNIVERSITY MEDICAL CENTER".

In other embodiments, the radio opaque element is an array of discrete units, wherein the units of the array may be the same or different, and wherein the discrete units are non-linear and have at least one vertex, wherein the vertex defines an angle of at least 15° and less than 165°, wherein the array of segments are in the shape of a geometric object or indicia. Discrete units are not connected together like the essentially continuous element described above. Suitable geometric objects and indicia are described above.

The radio opaque element may further comprise at least one additional additive comprising a colorant, a fluorescent agent, or a brightening agent. These additives can further assist in detecting the articles by providing optical detection methods, as described above.

Also disclosed herein are methods of preparing an absorbent medical article. In some embodiments, the method of preparing an absorbent medical article comprises providing a first absorbent layer with a first major surface and a second major surface, providing a continuous or discontinuous radio opaque adhesive article with a first major surface and a second major surface, contacting the first major surface of the continuous or discontinuous radio opaque adhesive article to the second major surface of the first absorbent layer, providing a second absorbent layer with a first major surface and a second major surface, and contacting the first major surface of the second absorbent layer to the second major surface of the continuous or discontinuous radio opaque adhesive article. The radio opaque adhesive article comprises an adhesive matrix and a radio opaque element comprising a radio opaque material. The radio opaque element comprises at least one segment that is non-linear and has at least one vertex, wherein the vertex defines an angle of at least 15° and less than 165°.

In some embodiments, the continuous or discontinuous radio opaque adhesive article further comprises a first carrier layer in contact with the first major surface and a second carrier layer in contact with the second major surface. In these embodiments, providing the continuous or discontinuous radio opaque adhesive article comprises removing the first carrier layer from the first major surface of the continuous or discontinuous radio opaque adhesive article. In these embodiments, the method further comprises, after contacting the first major surface of the continuous or discontinuous radio opaque adhesive article to the second major surface of the first absorbent layer, removal of the second carrier layer from second major surface of the continuous or discontinuous radio opaque adhesive article.

In some embodiments, the radio opaque adhesive article comprises a blend of a hot melt adhesive and a radio opaque material, and contacting the first major surface of the continuous or discontinuous radio opaque adhesive article to the second major surface of the first absorbent layer comprises hot melt coating.

In other embodiments, the radio opaque adhesive article comprises a polymeric adhesive matrix selected from a heat activated adhesive or a pressure sensitive adhesive, with a radio opaque material dispersed therein.

In some embodiments, the radio opaque adhesive article comprises a continuous layer of radio opaque material that is embossed to form a pattern on the radio opaque material layer surface. The pattern may be a positive pattern with protrusions that rise above the surface of radio opaque layer, or it may be a negative pattern with depressions in the surface of radio opaque layer. As described above, the embossed pattern comprises at least one element that is non-linear and has at least one vertex, wherein the vertex defines an angle of at least 15° and less than 165°.

In some embodiments, the radio opaque adhesive article comprises a multi-layer article comprising a first adhesive matrix layer, a continuous or discontinuous radio opaque layer, and a second adhesive matrix layer. As described above, the first adhesive matrix layer and the second adhesive matrix layer may be the same or different.

The articles of the disclosure may be more fully understood by referring to the attached figures. FIG. 1 shows a top view of article 100 with carrier layer 110 and continuous radio opaque article 120 with at least one vertex 130. In this embodiment, the radio opaque article has multiple vertices.

Figure 2:
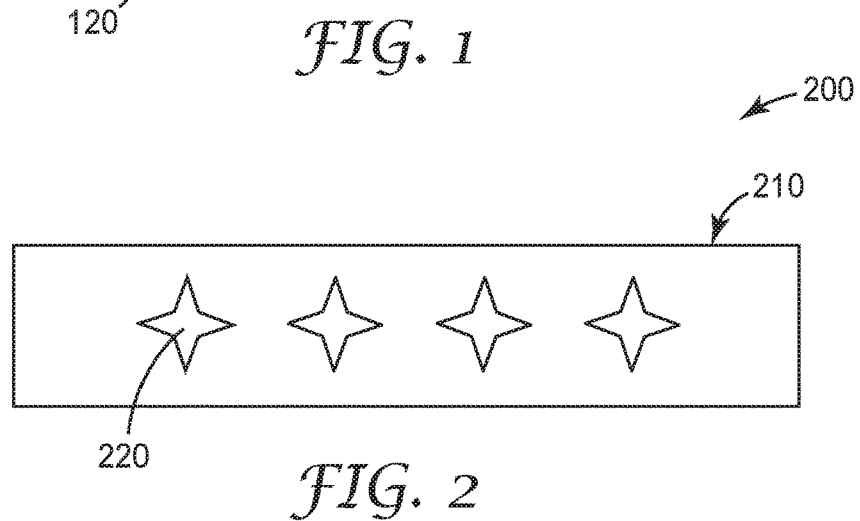
FIG. 2 is a top view of another embodiment of an article of the present disclosure.

FIG. 2 shows a top view of article 200 with carrier layer 210 and discrete radio opaque elements 220. The discrete radio opaque elements are shown as being star-shaped, but of course a wide variety of shapes are suitable.

Figure 3:
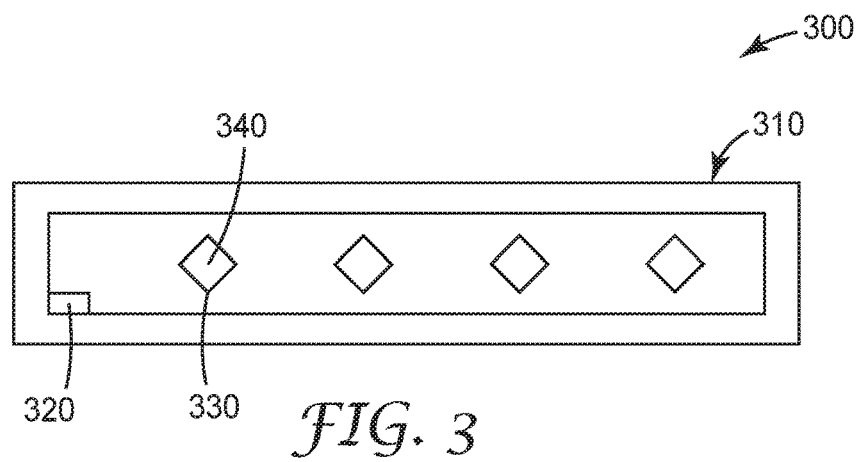
FIG. 3 is a top view of another embodiment of an article of the present disclosure.

FIG. 3 shows a top view of article 300 with carrier layer 310 and continuous radio opaque article 320 with cut out features 340 which have at least one vertex 330. In this article, instead of the element having a shape, the element is instead a shaped hole in a continuous layer.

The element is shown as being diamond-shaped, but of course a wide variety of shapes are suitable.

Figure 4:
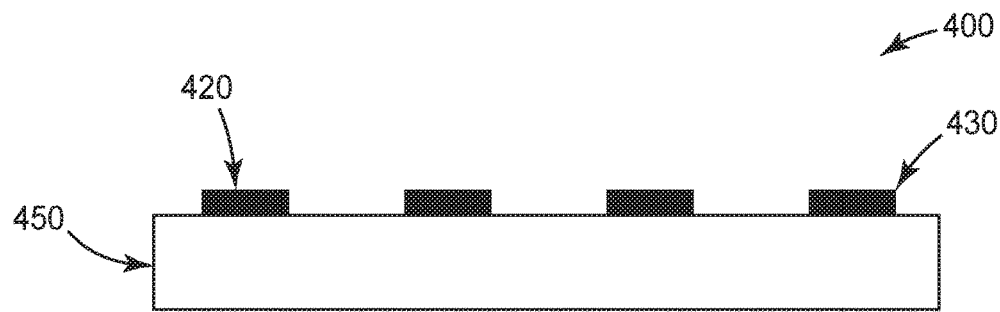
FIG. 4 is a cross sectional view of an embodiment of an absorbent medical article of the present disclosure.

FIG. 4 shows a cross sectional view of medical article 400 with absorbent substrate 450 and an array or radio opaque elements 420, where the radio opaque elements 420 have at least one vertex 430.

Figure 5:
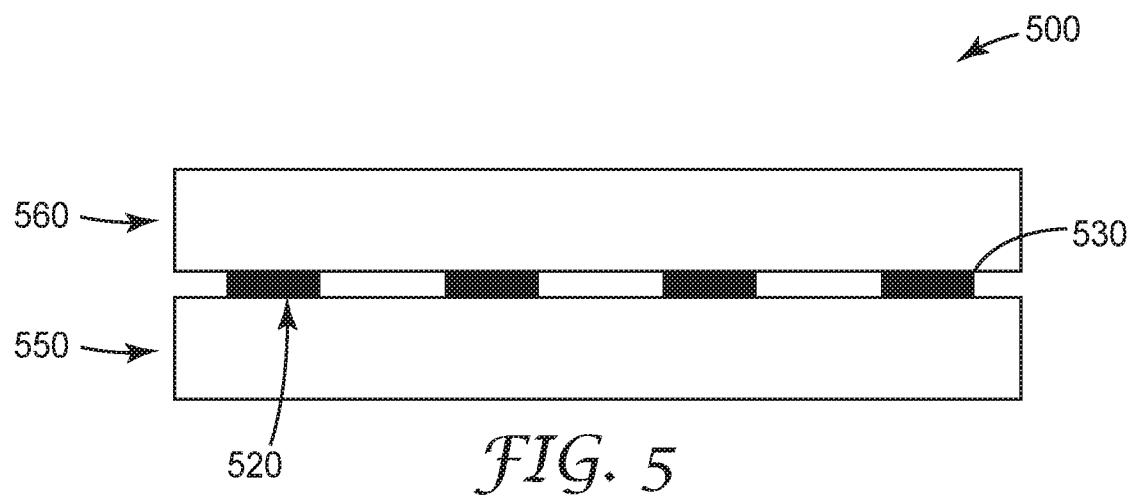
FIG. 5 is a cross sectional view of another embodiment of an absorbent medical article of the present disclosure.

FIG. 5 is a cross sectional view of medical article 500, which is the article of FIG. 4 with a second absorbent substrate 560. Second absorbent substrate 560 can be the same material as absorbent substrate 550, or it may be different. Absorbent substrate 560 may be a separate substrate, or it may be a section of absorbent substrate 550 that is folded over.

Figure 6:
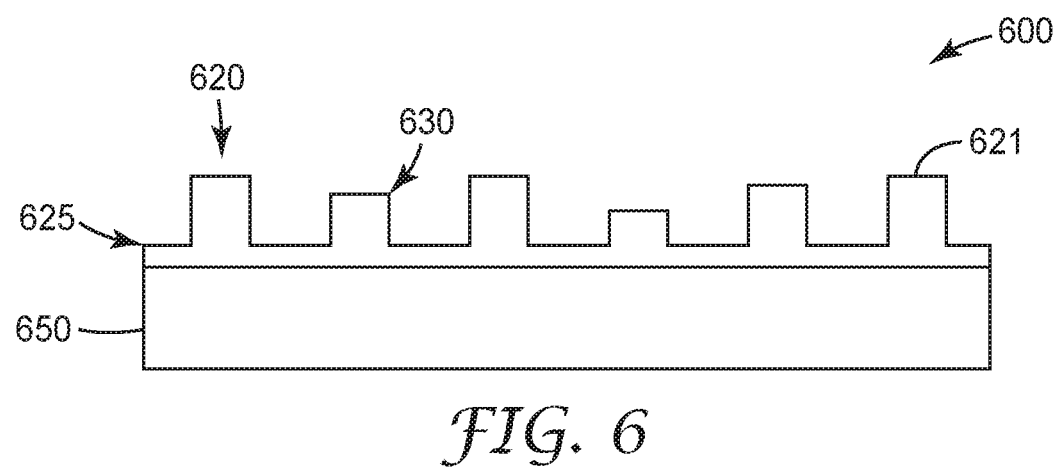
FIG. 6 is a cross sectional view of another embodiment of an absorbent medical article of the present disclosure.

FIG. 6 is a cross sectional view of medical article 600 with absorbent substrate 650 and continuous radio opaque layer 625 which comprises embossed features 620 and 621 of different size which have at least one point 630. In this embodiment the embossed features are protrusions that rise above the surface of radio opaque layer 625.

Figure 7:
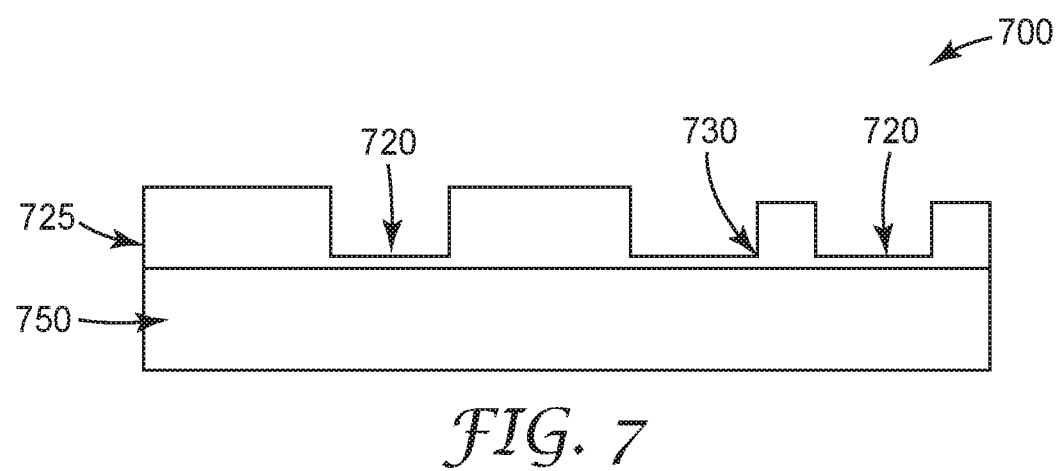
FIG. 7 is a cross sectional view of another embodiment of an absorbent medical article of the present disclosure.

FIG. 7 is a cross sectional view of medical article 700 with absorbent substrate 750 and continuous radio opaque layer 725 which comprises embossed features 720 and 721 of different size which have at least one point 730. In this embodiment the embossed features are depressions in the surface of radio opaque layer 725.

EXAMPLES

The resin used in the Examples was TECOTHANE TT-2095A-B40, which contains 40 weight percent barium sulfate and is available from Lubrizol Corp., Wickliffe, OH. Two separate film extrusion samples were made according to the manufacturer's processing recommendations for TECOTHANE TT-2095A-B40 pellets using an 8 inch (20.3 centimeter) drop die connected to a single screw extruder via a heated neck tube. Pigment was added to enhance visibility of the films. The samples were extruded onto a paper carrier, where the paper carrier was a polyethylene/vinyl acetate copolymer-coated supercalendered Kraft paper (1-80BKG-157 PE, Daubert Chemical Company, Chicago, IL).

The film extrusion of Example 1 was nipped onto a standard two-roll nip station, producing a flat film on the paper carrier. The film extrusion of Example 2 was made in the same manner except that a patterned rubber nip roller was used in place of the flat rubber nip roll, resulting in a hexagonally patterned extruded film on the paper carrier. The hexagons in the film were thicker than the remainder of the film. Both extruded films could be removed as desired from the paper carrier.

Discs were cut from the flat film of Example 1 and laminated to medical gauze with heat. The discs were stacked to provide varying levels of radiopacity, and specimens comprising stacks of 1, 2, 3, 4, 5, 10, and 20 radiopaque film discs were laminated to the gauze. Commercially available radiopaque thread was used as a comparison. X-ray radiographs of the gauze with laminated discs were taken from both the front (with discs) and back (without discs) sides. The discs were visible in both radiographs, and the radiopacity of each specimen was proportional to the number of film discs in the stack.

Samples were scored by comparison to the United States National Archives and Records Administration Monitor Adjustment Target, which has 11 shades ranging from white to black. The results are provided in Table 1.

TABLE 1

Scoring of radiopacity of laminated discs by comparison to Monitor Adjustment Target.

| Number of radiopaque film layers | Scoring |
|---|---|
| 1 | 3 |
| 2 | 3 |
| 3 | 4 |
| 4 | 4 |
| 5 | 4 |
| 10 | 4 |
| 20 | 5 |

The hexagonally patterned film of Example 2 was also X-rayed, and the hexagonal pattern was visible in the radiographs. Because the hexagons were thicker than the film surrounding them, they appeared darker in the radiographs.

These Examples demonstrate that man-made patterns can be formed of radiographic resins that when attached to medical substrates, render the substrate visible by X-ray and when the created patterns are clearly not human tissue related or shaped, easy detection of those medical substrates in the body is possible.

What is claimed is:

1. An adhesive article comprising:
   a first carrier layer with a first release surface;
   a second carrier layer with a second release surface; and
   a continuous or discontinuous radio opaque adhesive article located between the first release surface and the second release surface, wherein the continuous or discontinuous radio opaque adhesive article comprises a radio opaque element comprising a radio opaque material, wherein the radio opaque element comprises at least one segment that is non-linear and has at least one vertex, wherein the at least one vertex defines an angle of at least 15° and less than 165°.

2. The adhesive article of claim 1, wherein the radio opaque adhesive article comprises an adhesive layer comprising a polymeric adhesive matrix selected from a hot melt adhesive, a heat activated adhesive, or a pressure sensitive adhesive, with a radio opaque material dispersed therein.

3. The adhesive article of claim 1, wherein the radio opaque adhesive article comprises a multi-layer article comprising a first adhesive matrix layer, a continuous or discontinuous radio opaque layer, and a second adhesive matrix layer.

4. The adhesive article of claim 1, wherein the radio opaque material comprises a barium salt, a bismuth salt, a tungsten salt, or a combination thereof.

5. The adhesive article of claim 1, wherein the radio opaque adhesive article is a continuous element with an array of segments that are non-linear and have at least one vertex, wherein the at least one vertex defines an angle of at least 15° and less than 165°, wherein the array of segments are in the shape of a geometric object or indicia.

6. The adhesive article of claim 1, wherein the radio opaque adhesive article comprises an array of discrete units, wherein the units of the array may be the same or different, and wherein the discrete units are non-linear and have at least one vertex, wherein the at least one vertex defines an angle of at least 15° and less than 165°, wherein the array of segments are in the shape of a geometric object or indicia.

7. The adhesive article of claim 1, wherein the radio opaque element further comprises at least one additional additive comprising a colorant, a fluorescent agent, or a brightening agent.

8. The adhesive article of claim 1, wherein the radio opaque element comprises a protrusion extending from a surface of the radio opaque adhesive article.

9. An adhesive article, comprising:
a first carrier layer with a first release surface;
a second carrier layer with a second release surface; and
a radio opaque adhesive article located between the first release surface and the second release surface, wherein the radio opaque adhesive article comprises a radio opaque element comprising a radio opaque material, wherein the radio opaque element comprises at least one vertex that defines an angle of at least 15° and less than 165°.

10. The adhesive article of claim 9, wherein the radio opaque adhesive article comprises an adhesive layer.

11. The adhesive article of claim 9, wherein the radio opaque adhesive article comprises a first adhesive matrix layer, a radio opaque layer, and a second adhesive matrix layer.

12. The adhesive article of claim 9, wherein the radio opaque material comprises a barium salt, a bismuth salt, or a tungsten salt, or a combination thereof.

13. The adhesive article of claim 9, wherein the radio opaque adhesive element comprises a protrusion extending from a surface of the radio opaque adhesive article.

14. The adhesive article of claim 9, wherein the radio opaque element comprises a continuous radio opaque element.

15. The adhesive article of claim 9, wherein the radio opaque adhesive article comprises a plurality of discrete radio opaque elements including the radio opaque element.

16. The adhesive article of claim 9, wherein the radio opaque element further comprises at least one additional additive comprising a colorant, a fluorescent agent, or a brightening agent.

17. The adhesive article of claim 10, wherein the adhesive layer comprises a polymeric adhesive matrix selected from a hot melt adhesive, a heat activated adhesive, or a pressure sensitive adhesive, with a radio opaque material dispersed therein.

* * * * *